(12) United States Patent
Jeong

(10) Patent No.: US 12,108,974 B2
(45) Date of Patent: *Oct. 8, 2024

(54) SYSTEMS AND METHODS FOR RENAL DENERVATION

(71) Applicant: DEEPQURE INC., Seoul (KR)

(72) Inventor: Chang Wook Jeong, Seoul (KR)

(73) Assignee: DEEPQURE INC., Seoul (KR)

( * ) Notice: Subject to any disclaimer, the term of this patent is extended or adjusted under 35 U.S.C. 154(b) by 1069 days.

This patent is subject to a terminal disclaimer.

(21) Appl. No.: 17/012,534

(22) Filed: Sep. 4, 2020

(65) Prior Publication Data

US 2020/0397496 A1 Dec. 24, 2020

Related U.S. Application Data

(63) Continuation of application No. 15/258,167, filed on Sep. 7, 2016, now Pat. No. 11,259,859.

(51) Int. Cl.
*A61B 18/14* (2006.01)
*A61B 18/08* (2006.01)
*A61B 18/00* (2006.01)

(52) U.S. Cl.
CPC ........ *A61B 18/082* (2013.01); *A61B 18/1492* (2013.01); *A61B 2018/00404* (2013.01); *A61B 2018/00434* (2013.01); *A61B 2018/00791* (2013.01); *A61B 2018/00875* (2013.01); *A61B 2018/1407* (2013.01); *A61B 2018/142* (2013.01); *A61B 2018/1435* (2013.01); *A61B 2018/1467* (2013.01); *A61B 2018/1475* (2013.01)

(58) Field of Classification Search
CPC .......... A61B 18/1475; A61B 2018/142; A61B 2018/1435; A61B 2018/1407; A61B 2018/00404; A61B 18/082; A61B 2018/00434

See application file for complete search history.

(56) References Cited

U.S. PATENT DOCUMENTS

| | | | |
|---|---|---|---|
| 3,955,578 A * | 5/1976 | Chamness | A61B 17/32056 606/47 |
| 5,486,183 A | 1/1996 | Middleman et al. | |
| 6,050,995 A * | 4/2000 | Durgin | A61B 18/14 606/50 |
| 6,162,184 A | 12/2000 | Swanson et al. | |
| 6,978,174 B2 | 12/2005 | Gelfand et al. | |
| 8,150,520 B2 | 4/2012 | Demarais et al. | |
| 8,473,067 B2 | 6/2013 | Hastings et al. | |
| 8,740,849 B1 | 6/2014 | Fischell et al. | |
| 2003/0018330 A1 | 1/2003 | Swanson et al. | |
| 2004/0193151 A1* | 9/2004 | To | A61B 18/1492 606/41 |
| 2005/0015083 A1 | 1/2005 | Koblish et al. | |
| 2006/0009759 A1 | 1/2006 | Chrisitian et al. | |

(Continued)

FOREIGN PATENT DOCUMENTS

| | | |
|---|---|---|
| KR | 10-1370048 B1 | 2/2014 |
| KR | 10-1399555 B1 | 5/2014 |

*Primary Examiner* — Jaymi E Della
(74) *Attorney, Agent, or Firm* — Merchant & Gould P.C.

(57) ABSTRACT

Provided is a catheter including a shaft having a distal end and a loop disposed near the distal end and configured to curl around a tissue and receive, via the shaft, energy to denervate at least a portion of the tissue.

19 Claims, 9 Drawing Sheets

(56) References Cited

U.S. PATENT DOCUMENTS

| | | | |
|---|---|---|---|
| 2006/0030919 A1* | 2/2006 | Mrva | A61N 1/0556 |
| | | | 607/118 |
| 2006/0041277 A1* | 2/2006 | Deem | A61N 1/36117 |
| | | | 607/3 |
| 2010/0137860 A1 | 6/2010 | Demarais et al. | |
| 2011/0112400 A1 | 5/2011 | Emery et al. | |
| 2012/0259269 A1 | 10/2012 | Meyer | |
| 2014/0107639 A1 | 4/2014 | Zhang et al. | |
| 2014/0303618 A1 | 10/2014 | Wu et al. | |
| 2015/0025524 A1 | 1/2015 | Nabutovsky | |
| 2015/0141810 A1* | 5/2015 | Weadock | A61N 7/02 |
| | | | 606/49 |
| 2015/0224326 A1 | 8/2015 | Toth et al. | |
| 2016/0089198 A1 | 3/2016 | Arya et al. | |
| 2016/0113711 A1 | 4/2016 | Osypka et al. | |
| 2016/0143642 A1 | 5/2016 | Wright | |
| 2016/0256218 A1 | 9/2016 | Gandhi et al. | |
| 2017/0202467 A1 | 7/2017 | Zitnik et al. | |

\* cited by examiner

[Fig. 1]
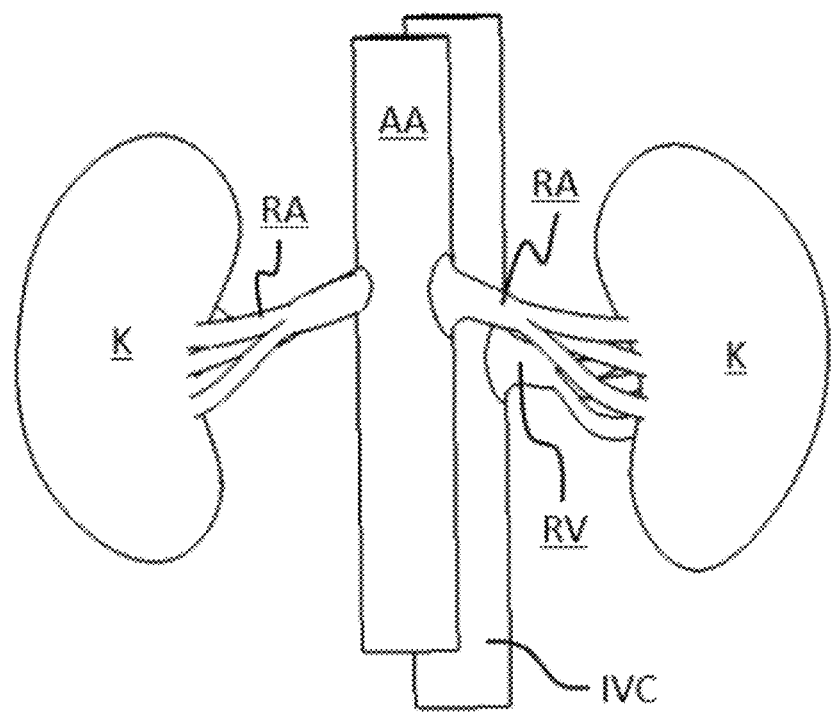
[Fig. 2A]
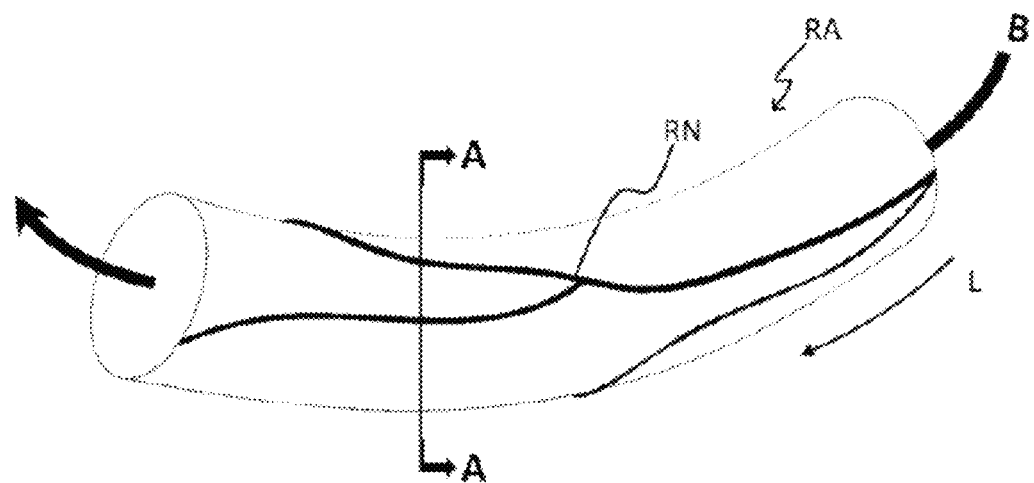

[Fig. 2B]
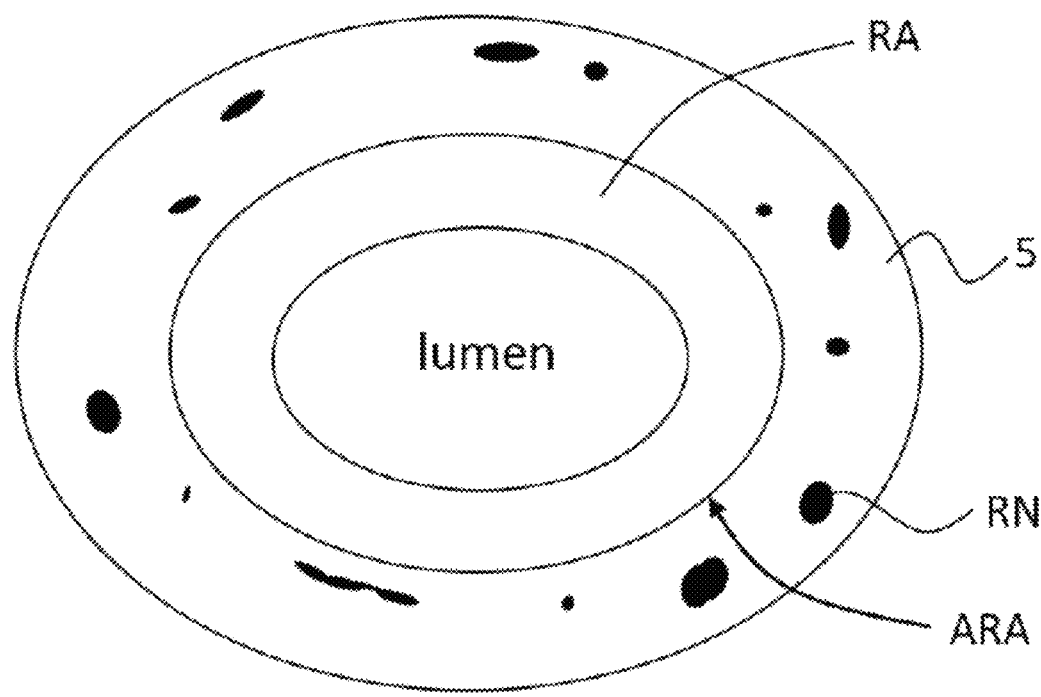
[Fig. 3]
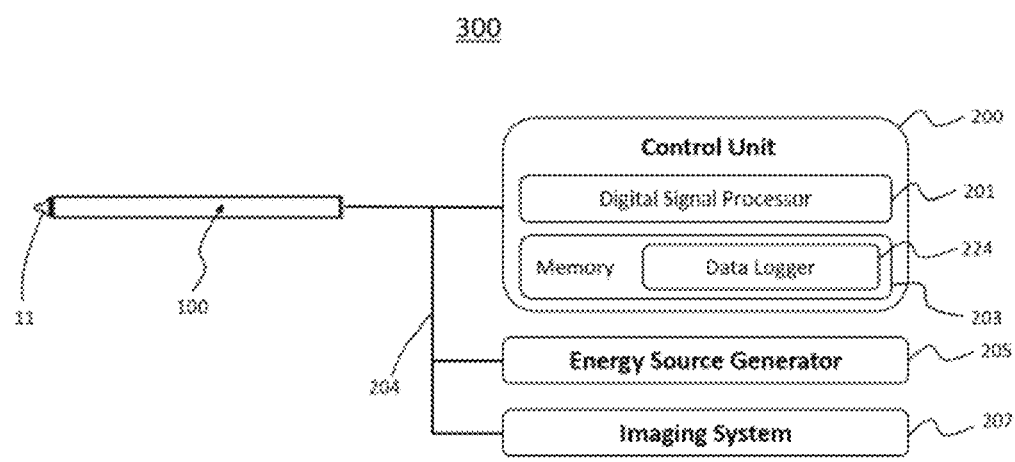

[Fig. 4]
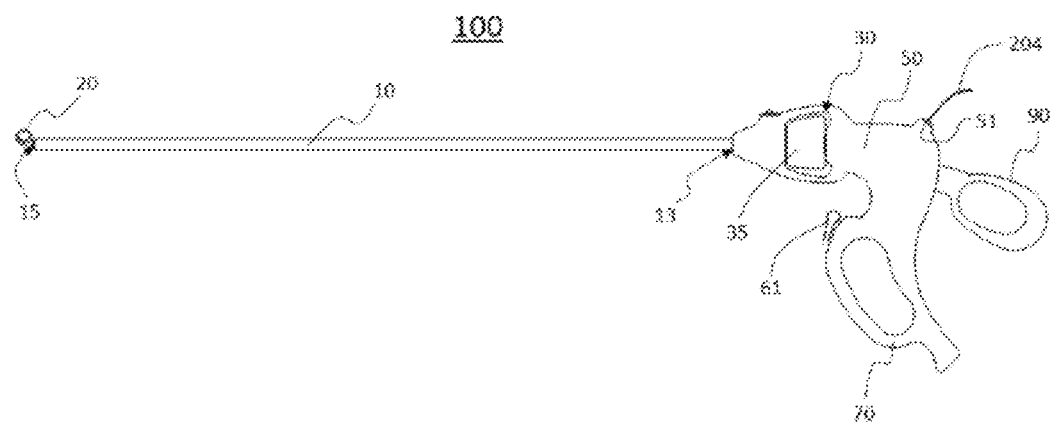
[Fig. 5]
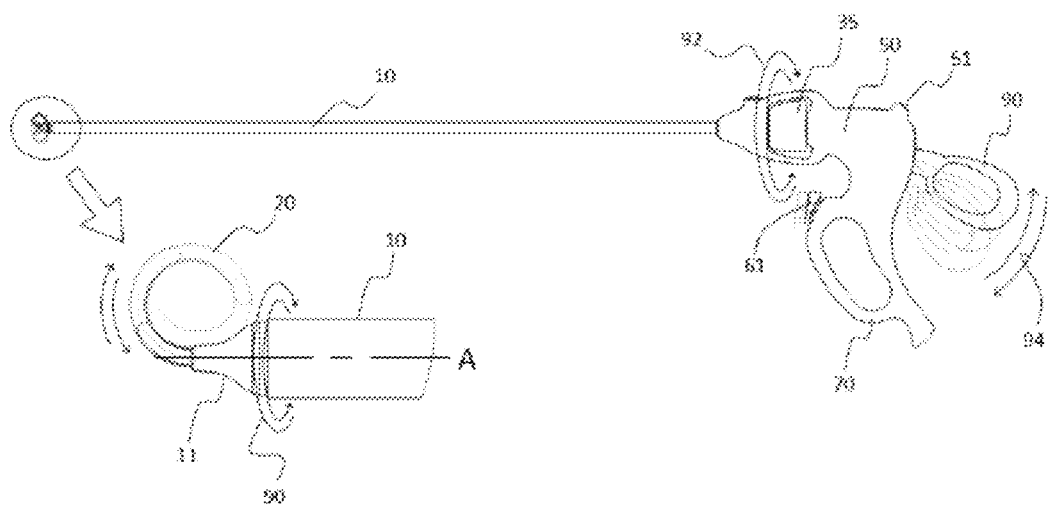

[Fig. 6A]
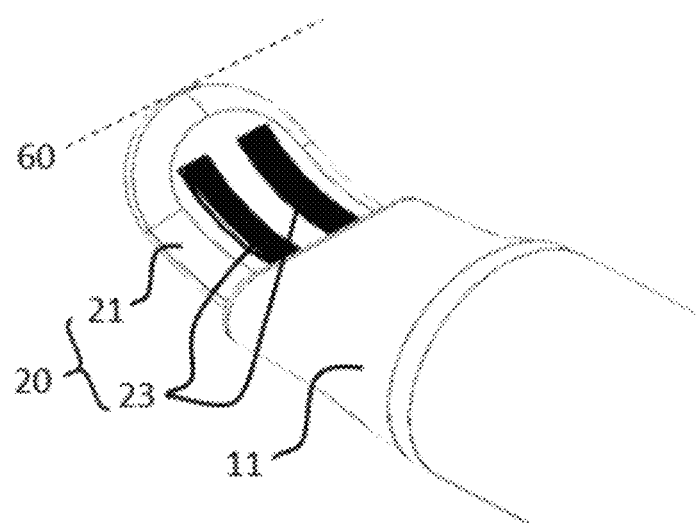
[Fig. 6B]
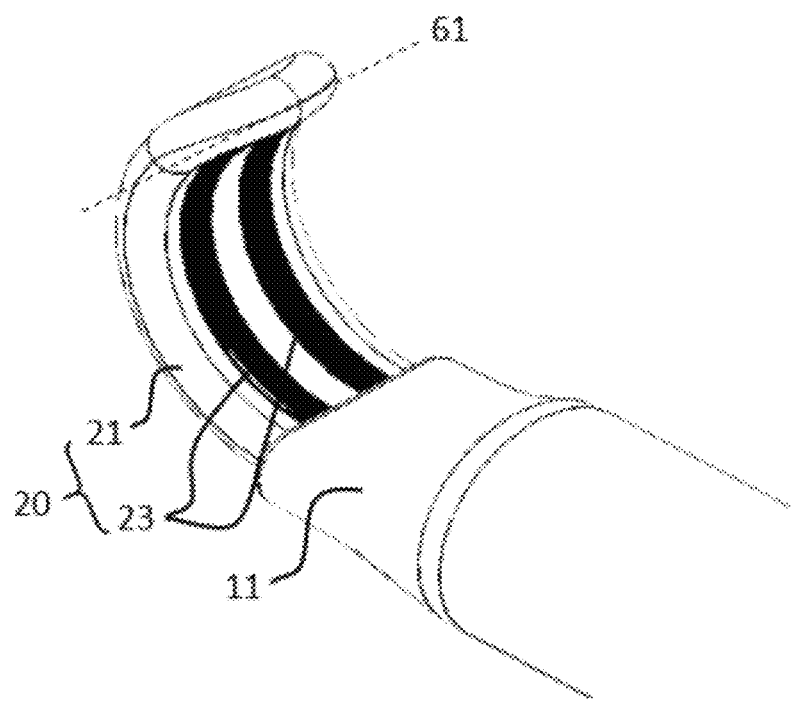

[Fig. 6C]
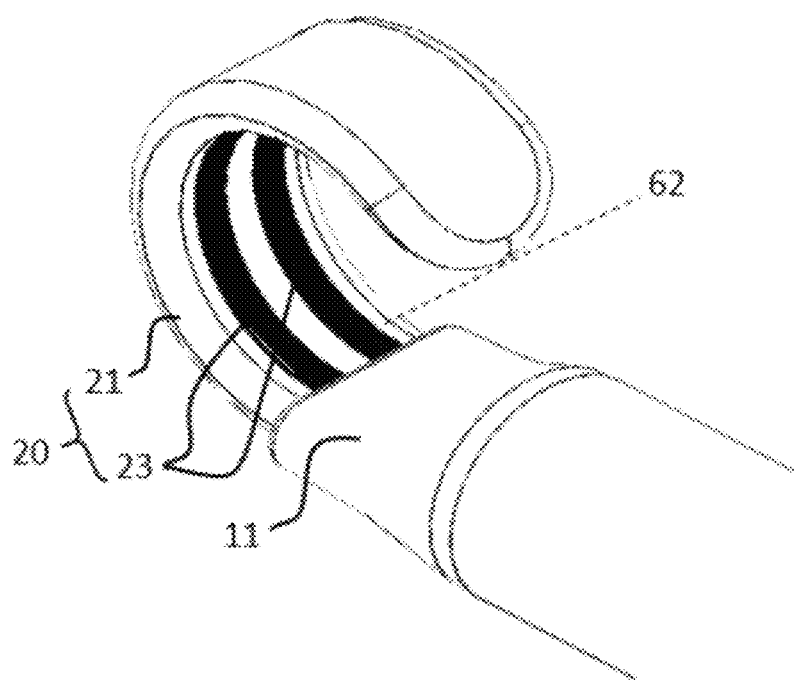
[Fig. 6D]
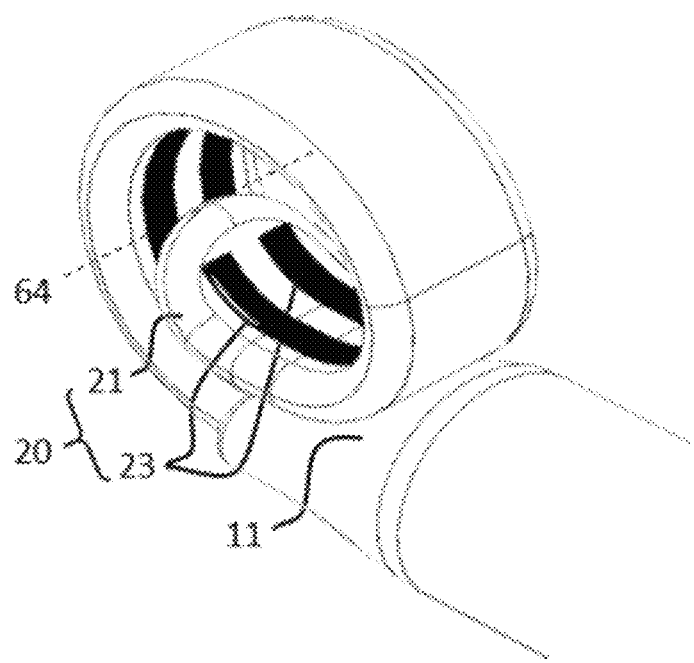

[Fig. 7A]
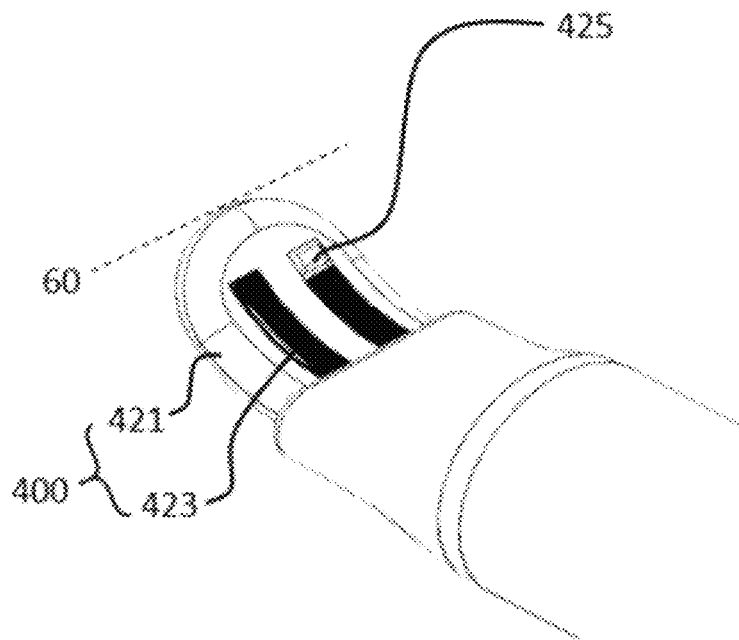
[Fig. 7B]
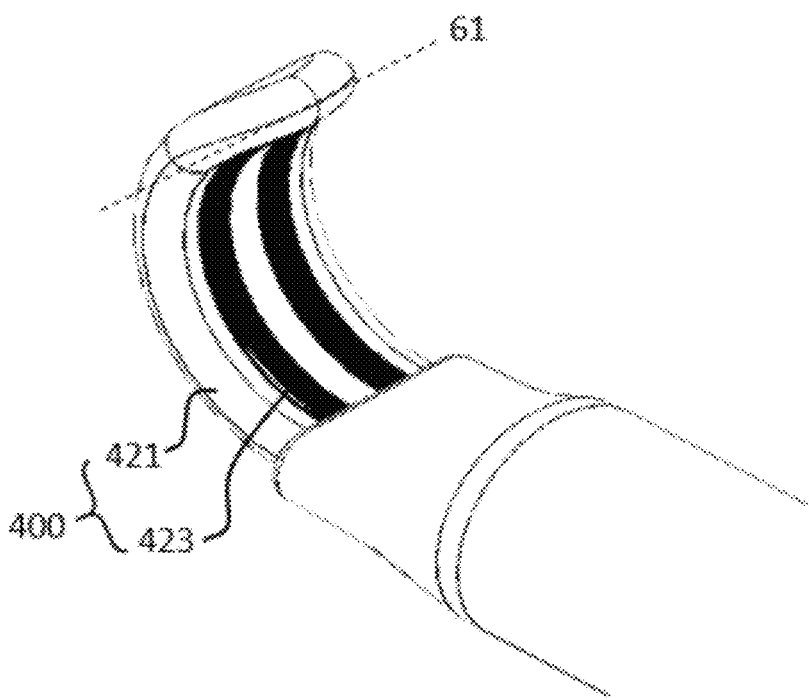

[Fig. 7C]
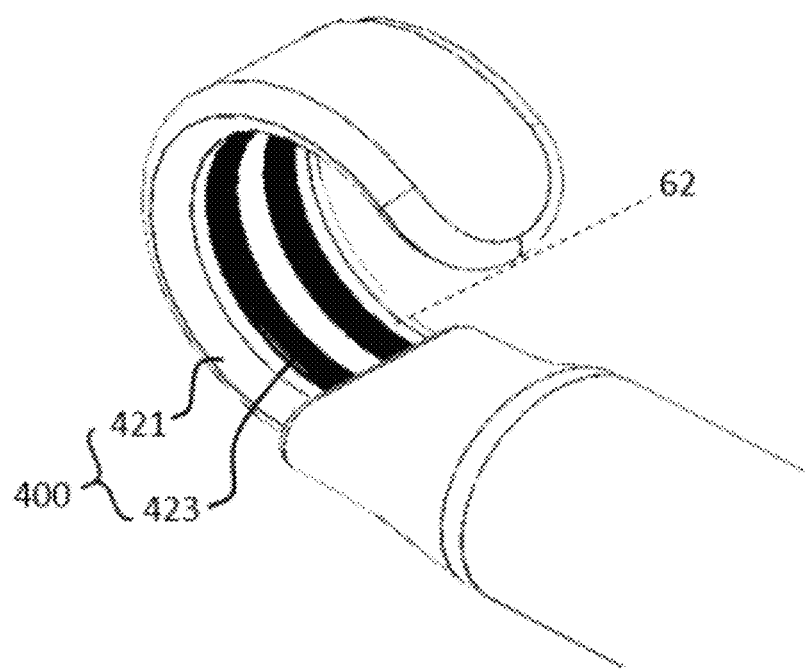
[Fig. 7D]
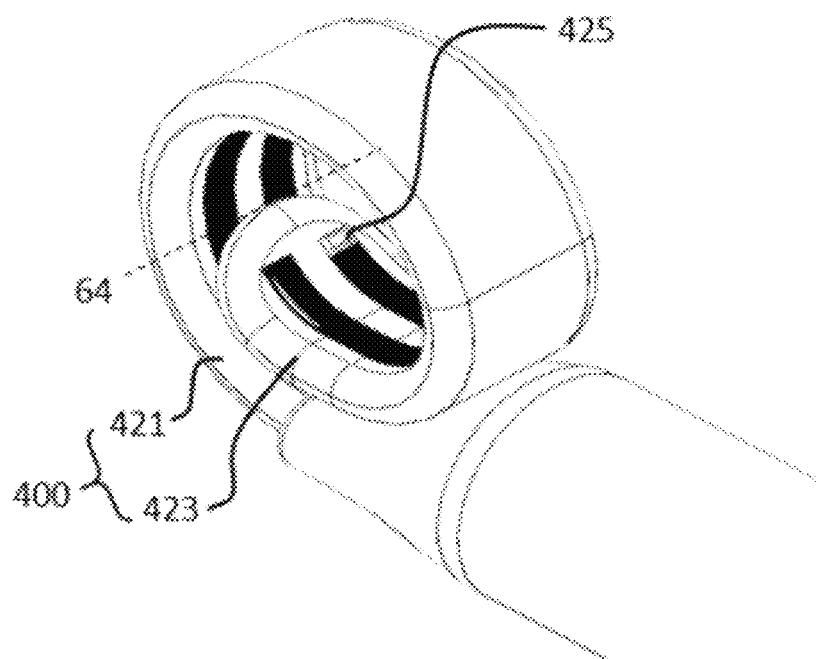

[Fig. 8]
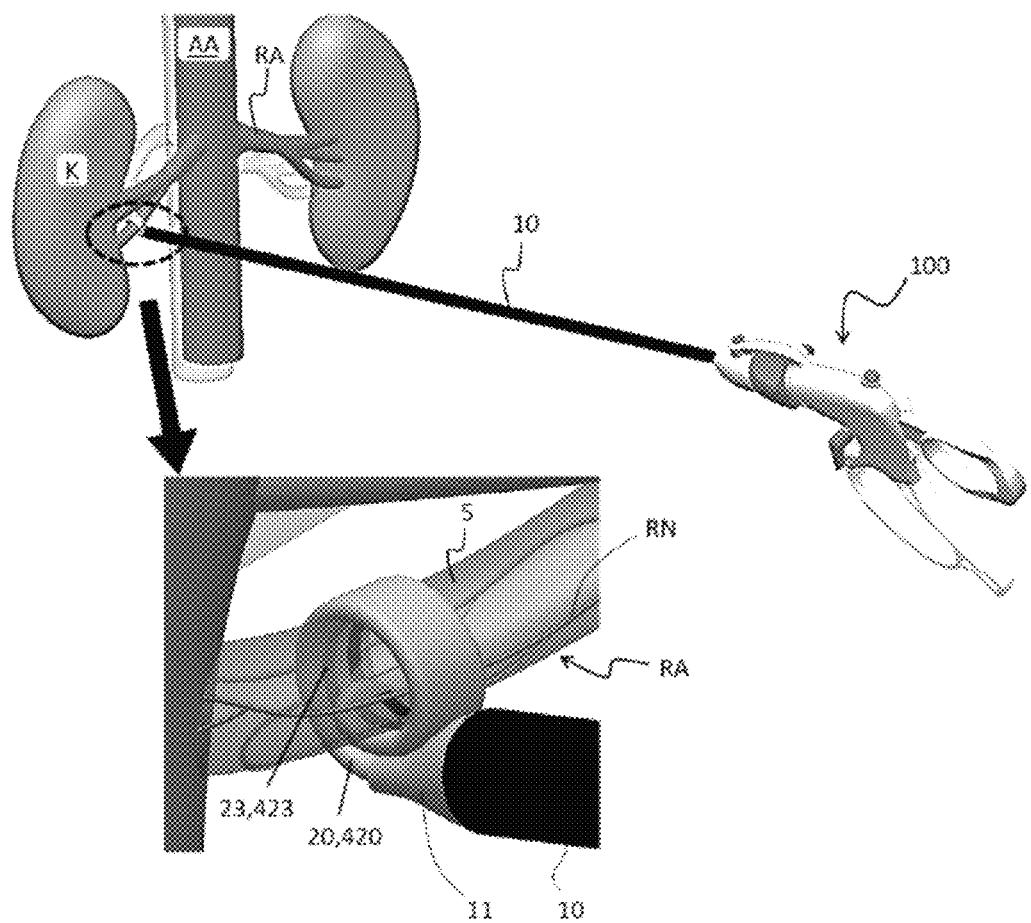

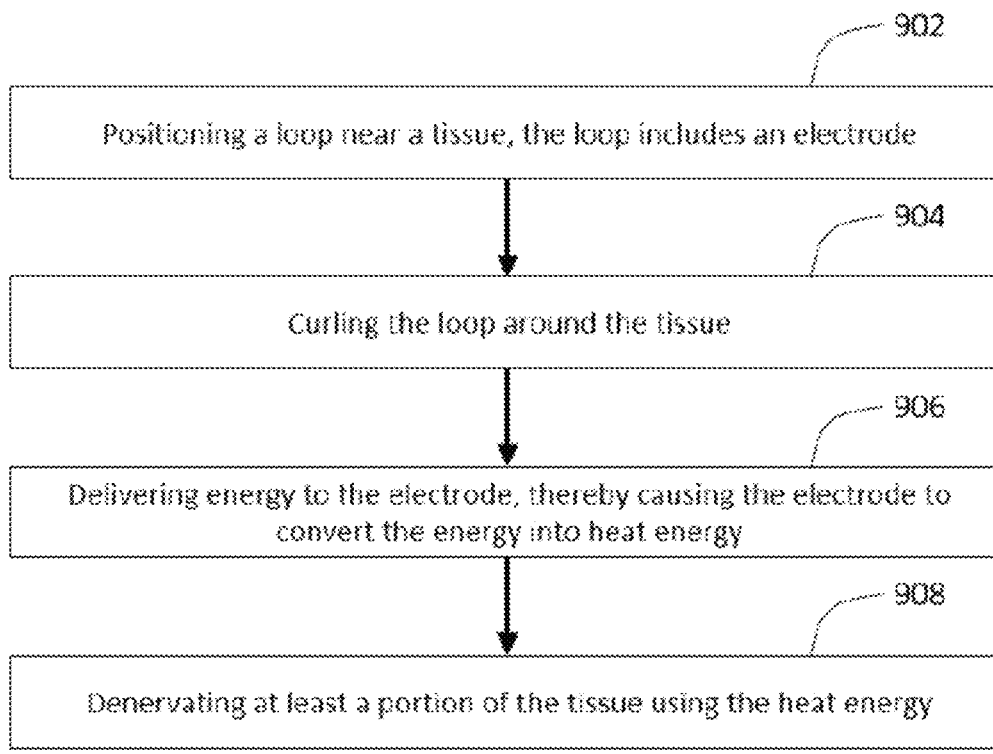
[Fig. 9]

SYSTEMS AND METHODS FOR RENAL DENERVATION

CROSS REFERENCE TO RELATED APPLICATION(S)

This application is a continuation application of U.S. application Ser. No. 15/528,167 filed on Sep. 7, 2016, now U.S. Pat. No. 11,259,859.

FIELD OF THE INVENTION

The present disclosure relates to renal denervation, and more particularly to catheter apparatus and methods for renal denervation of human patients.

DESCRIPTION OF THE RELATED ART

High blood pressure is often difficult to control. Resistant hypertension is defined as a blood pressure that remains above goal despite the concomitant use of full doses of three or more antihypertensive drugs from different classes. One approach to treat patients with resistant hypertension is renal denervation for blocking sympathetic nerve around the renal artery of the patients.

Recently, it has been reported that renal denervation for blocking sympathetic nerve around the renal artery using percutaneous catheter can be effective for lowering blood pressure in patients with resistant hypertension. Besides, this renal denervation strategy has gained attention for the usefulness in the treatment of patients with arrhythmia and cardiac failure.

However, in the existing approaches for performing renal denervation, it is difficult to destruct effectively renal nerves since most of the renal nerves are distributed far away from the intima of renal artery and the conventional percutaneous catheters are designed to destruct the renal nerves from inner side of the renal artery. Also, the conventional percutaneous catheters may severely damage the intima of the renal artery as well as the adventitia of the renal artery and, in some cases, may cause angiostenosis.

Therefore, there is a need for new catheters that can help the physicians effectively destruct the renal nerves and methods for performing renal denervation without damaging the renal artery and nearby organs/tissues.

SUMMARY OF THE INVENTION

The present disclosure provides catheter apparatus and methods for renal denervation that effectively and completely destruct a circumferential tissue of renal artery such as renal nerves.

In accordance with an aspect of the present disclosure, catheter apparatus for renal denervation includes: a shaft having a distal end; and a loop disposed near the distal end and configured to curl around a tissue and receive, via the shaft, energy to denervate at least a portion of the tissue.

In accordance with another aspect of the present disclosure, a method for renal denervation using a catheter having a loop includes positioning the loop near a tissue, the loop includes an electrode; curling the loop around the tissue; delivering energy to the electrode, thereby causing the electrode to convert the energy into heat energy; and denervating at least a portion of the tissue using the heat energy.

BRIEF DESCRIPTION OF THE DRAWINGS

The objects, features and advantages of the present disclosure will be more apparent from the following detailed description in conjunction with the accompanying drawings, in which:

FIG. 1 illustrates anatomy of a human kidney.

FIG. 2A is a schematic diagram of human renal nerves and renal artery.

FIG. 2B is a cross sectional view of human renal artery and renal nerves.

FIG. 3 is a schematic block diagram of a catheter system for renal denervation according to embodiments of the present invention.

FIG. 4 is a side elevational view of a catheter according to embodiments of the present invention.

FIG. 5 illustrates an exemplary operation of a catheter according to embodiments of the present invention.

FIG. 6A to 6D and FIG. 7A to 7D illustrate loops of the catheter in FIG. 4 according to embodiments of the present invention.

FIG. 8 is a schematic diagram of a catheter, illustrating renal denervation using the catheter according to embodiments of the present invention.

FIG. 9 is a flow chart illustrating exemplary steps that may be carried out to denervate renal nerves according to embodiments of the present invention.

DETAILED DESCRIPTION OF EXEMPLARY EMBODIMENTS

Exemplary embodiments of the present disclosure are described with reference to the accompanying drawings in detail. The same reference numbers are used throughout the drawings to refer to the same or like parts. Detailed descriptions of well-known functions and structures incorporated herein may be omitted to avoid obscuring the subject matter of the present disclosure.

Components, or nodes, shown in diagrams are illustrative of exemplary embodiments of the invention and are meant to avoid obscuring the invention. It shall also be understood that throughout this discussion that components may be described as separate functional units, which may comprise sub-units, but those skilled in the art will recognize that various components, or portions thereof, may be divided into separate components or may be integrated together, including integrated within a single system or component.

Reference in the specification to "one embodiment," "preferred embodiment," "an embodiment," or "embodiments" means that a particular feature, structure, characteristic, or function described in connection with the embodiment is included in at least one embodiment of the invention and may be in more than one embodiment. The appearances of the phrases "in one embodiment," "in an embodiment," or "in embodiments" in various places in the specification are not necessarily all referring to the same embodiment or embodiments.

The terms and words used in the following description and claims are not limited to the bibliographical meanings, but, are merely used by the inventor to enable a clear and consistent understanding of the present disclosure.

In the present disclosure, the terms such as "include" and/or "have" may be construed to denote a certain characteristic, number, step, operation, constituent element, component or a combination thereof, but may not be construed to exclude the existence of or a possibility of addition of one or more other characteristics, numbers, steps, operations, constituent elements, components or combinations thereof.

FIG. 1 illustrates a common human renal anatomy. As depicted, the kidneys K are supplied with oxygenated blood by renal arteries RA, which are connected to the heart by the abdominal aorta AA. Deoxygenated blood flows from the kidneys to the heart via renal veins RV and the inferior vena cava IVC.

FIG. 2A illustrates a portion of human renal artery RA and renal nerves RN. FIG. 2B illustrates a cross-sectional view taken along the radial plane A-A of FIG. 2A.

As depicted, the renal artery RA has a lumen through which the blood B flows. The renal nerves RN are located in proximity to the adventitia of the renal artery ARA and run along the renal artery RA in a lengthwise direction L. More specifically, renal nerves RN are situated in a circumferential tissue 5 surrounding the outer wall of the renal artery RA and the circumferential tissue 5 may include other tissue, such as lymphatics and capillaries.

In the conventional approaches based on applying denervation energy to destroy the renal nerves RN, a catheter is inserted into the lumen and delivers heat energy to denervate the target renal nerves RN. During this process, the denervation energy may damage the adventitia ARA of renal artery RA before it reaches the renal nerves RN. Furthermore, a portion of the denervation energy may be absorbed by the adventitia of the renal artery ARA, reducing the efficiency in utilizing the energy. Accordingly, it may be more effective and safer to denervate from outside of the renal artery RA (i.e., apply energy from outside of RA) than to denervate from inside of the renal artery RA (i.e., apply energy from inside of RA).

FIG. 3 is a schematic block diagram of a catheter system 300 for renal denervation according to embodiments of the present invention. As depicted, the catheter system 300 includes: a catheter apparatus 100 having a distal portion 11 which may make a contact with a target tissue and/or be disposed in proximity to the target tissue for treatment; a control unit 200 for controlling one or more components of the system 300; an energy source generator (ESG) 205 for supplying energy to the target tissue through the distal portion 11 of the catheter apparatus 100; an imaging system 207 for processing visual images and displaying the images to the users; and wires/cables/buses 204 that connect the components of the system 300 to each other for communication.

The control unit 200 may collectively refer to one or more components for controlling various components of the catheter system 300. In embodiments, the control unit 200 may include a digital signal processor (DSP) 201, such as CPU, and a memory 203. The memory 203 may store various data and include, but are not limited to: magnetic media such as hard disks, floppy disks, and magnetic tape; optical media such as CD-ROMs and holographic devices; magneto-optical media; and hardware devices that are specially configured to store or to store and execute program code, such as application specific integrated circuits (ASICs), programmable logic devices (PLDs), flash memory devices, and ROM and RAM devices.

In embodiments, a data logger 224 may be included in the memory 203 and store data (e.g., temperature of the target tissue) measured by the catheter 100 during the denervation procedure. It is note that the memory 203 may be located outside the control unit 200 and coupled to the control unit 200 via a wire/cable 204.

It is noted that the control unit 200 may be a computer, a server, or any other suitable computing facility and include other components, such as printer, input device (such as keyboard and mouse), scanner, display device, and a network interface.

In embodiments, the distal portion 11 may include denervation element(s) and optionally an endoscope or some other type of imaging device, coupled to an imaging system 207, to provide images of the target tissue using suitable imaging techniques. The imaging device may allow the operator/physician to visually identify the region being ablated/denervated, to monitor the progress of the ablation/denervation in real time, and to address safety concerns during operation.

FIG. 4 is a side elevational view of a catheter apparatus 100 according to embodiments of the present invention. As depicted, the catheter apparatus 100 comprises a shaft 10, a loop 20, a holder 30, a slider 35, a butt 50, a handle 70 and a loop control 90.

The shaft 10 has a proximal end 13 coupled to the holder 30 and a distal end 15 removably connected to the distal portion 11 of the catheter apparatus 100. The shaft 10 has a shape of tube, forming a channel that extends from the proximal end 13 to the distal end 15, and is dimensioned to allow a stylet and/or a wire(s) to pass therethrough. The distal portion 11 may form a passage through which the loop 20 travels, as explained in detail below.

In embodiments, the shaft 10 may be made of silicone, polyurethane (PU), Pebax, or a combination of PU and silicone, or some other biocompatible polymers and/or metallic materials. The shaft 10 may be sufficiently large enough to house an imaging device, such as an endoscope, as well as components for ablation/denervation. In embodiments, the shaft 10 may include electrical wires/cables that run from the energy source generator 204 to the electrodes on the loop 20. In embodiments, the shaft 10 may include wires/cables for providing electrical energy to the endoscope and transmitting visual images from the endoscope to the control unit 200. In embodiments, the shaft 10 may be dimensioned to provide safe and easy treatment of the target tissue with minimal percutaneous access site on the patient, for example, on the abdominal region.

In embodiments, the loop 20 may be removably coupled to the distal end 15 of the shaft 10 and mechanically connected to the shaft 10.

The holder 30 is connected to the proximal end 13 of the shaft 10. More specifically, the holder 30 may have a structure for accepting the proximal end 13 of the shaft 10 therein and be electrically coupled to the proximal end 13. In embodiments, a slider 35 may be rotatably coupled to the holder 30 and the operator may rotate the slider 35 to engage (or disengage) the shaft 10 to (or from) the holder 30.

In embodiments, the holder 30 may include the butt 50 and a terminal 51 disposed on one side of the butt 50. The terminal 51 may receive various types of energy from the energy source generator 205 via the wire/cable 204 and the energy is delivered from the terminal 51 to the loop 20 via suitable wires/cables running through the shaft 10. In embodiments, the energy may be, but not limited to, at least one of a radio-frequency (RF) energy, electrical energy, laser energy, ultrasonic energy, high-intensity focused ultrasound (HIFU) energy, cryogenic energy, and thermal energy. Energy may be delivered to the loop 20, simultaneously or sequentially, or selectively. For selective delivery, a clinician can select, via a user interface of the energy source generator 205, such as an RF generator, a specific electrode to be utilized in the denervation process, where the electrode is disposed in the loop 20.

The handle 70 may extend from the butt 50. The handle may have a vacant space (hole) into which the operator may insert his finger(s) to have a firm grip of the holder 30.

A push-button 61 may be disposed on another side of the butt 50 or one side of the handle 70. The push-button 61 is operated by the operator to control the energy flow to the loop 20.

The loop control 90 may be hinged on the butt 50 or the handle 70. The loop control 90 may also have a vacant space (hole) in which the operator's thumb can be inserted. As described below, the operator may control the loop control 90 to coil/uncoil the loop 20.

FIG. 5 illustrates an example of an operation of a catheter according to an embodiment of the present invention. As shown in the FIG. 5, the slider 35 may be rotated up to about 360 degrees about the longitudinal axis A of the shaft 10. A rotational direction of the slider 35 may be bidirectional or unidirectional. As the slider 35 rotates, as indicated by the arrows 92, the loop 20 may also rotate around the longitudinal axis A of the shaft 10, as indicated by the arrows 90. Thus, a rotation of the loop 20 about the longitudinal axis of the shaft 10 may be controlled by the rotation of the slider 35.

In embodiments, when moved forward/backward (or upward/downward) by the operator's finger, as indicated by arrows 94, the loop control 90 mechanically controls the loop 20, where the loop control 90 may be designed to operate in various modes. In one mode, as the loop control moves forward (or downward), the loop 20, which is originally rolled, may be unrolled to a straight segment and extend along the longitudinal axis A of the shaft 10. As the loop control 90 moves backward (or upward), the loop 20 is rolled to its original shape. In this mode, the operator may bring the loop 20 near the target tissue or renal artery RA and move the loop control 90 backward to curl the loop 20 around the target tissue or renal artery RA.

In another mode, the loop 20 may be retracted into the shaft 10. As the loop control 90 is moved forward (or downward), the loop 20 may emerge from the distal portion and become a straight segment or curl into a semi-circle. As the loop control 90 is moved backward (or upward), the loop 20 may curl around the target tissue or renal artery RA.

FIG. 6A to FIG. 6D show a loop that curls as it emerges from the shaft 10 of the catheter apparatus according to embodiments of the present invention. As depicted, the loop 20 includes a body 21 and one or more electrodes 23 disposed on the body 21. The loop 20 may remain inside the shaft 10 and distal portion 11 (retracted position) when the loop control 90 is in the neutral position. As the operator moves the loop control 90 forward (or downward), the loop 20 emerges from the distal portion 11, forming a curved segment. As depicted in FIG. 6A to 6D, the loop 20 curls as the tip of the loop 20 proceeds from the position 60 toward the position 64.

In embodiments, the body 21 may be made of a flexible material. In embodiments, the body 21 may be made of thermally non-conductive elastic material so that the energy delivered to the electrodes 23 is localized only to a portion(s) of the tissue that the electrodes 23 contact. As the localized energy is used to denervate the renal nerves RN (shown in FIG. 3), the potential damage caused by the loop 20 to the tissue nearby the renal nerves RN may be significantly reduced during operation.

In embodiments, the loop 20 may be flexible and deformable to curl around a renal artery as discussed in conjunction with FIG. 8. The loop 20 may be designed for two different operational modes. In the first mode, the loop 20 may remain flat when the loop 20 is brought into proximity to the target tissue, such as the circumferential tissue 5 of the renal artery. Then, the operator may manipulate the loop control 90 to curl the loop 20 around the circumferential tissue 5 and perform denervation. Upon completing the denervation, the operator may release the loop control 90 to uncurl loop 20. In the second mode, the loop 20 may remain curled when the distal portion 11 is brought into proximity to the target tissue. Then, the operator may manipulate the loop control 90 to uncurl the loop 20, position the loop 20 around the target tissue, release the loop control 90 to curl the loop 20 around the renal artery and perform denervation.

In embodiments, the electrodes 23 may be disposed on the inner side of the body 21 so that the electrodes 23 may contact the circumferential tissue 5 when the loop 20 curls around the circumferential tissue 5. In embodiments, the electrodes 23 may extend along the longitudinal direction of the body 21 and be arranged in parallel to each other. In one embodiment, the body 21 may be formed of dielectric material and the electrodes 23 may be formed on the inner surface of the body 21. In embodiments, the body 21 may have a groove or a channel on the inner surface of the body 21 and the electrodes 23 may be formed by filling electrically conductive material in the groove or the channel.

In another embodiment, the body 21 may be formed of electrically conducting material and the entire surface of the body 21 may be covered with dielectric material except the location where the electrodes 23 are to be located. In embodiments, a dielectric body may be disposed between the two electrodes 23 to electrically isolate the electrodes 23 from each other.

In embodiments, the electrodes 23 may be formed of electrically-conductive elastic material so that they can deform along with the body 21 as the body 21 is curled/uncurled. In embodiments, the electrodes 23 may contact the circumferential tissue 5 surrounding the outer surface of the renal artery and generate heat energy when electrical energy, such as RF energy, is supplied, where the heat energy may be used to denervate the renal nerve RN.

In FIG. 6A to 6D, only two electrodes 23 are shown. However, it should be apparent to those of ordinary skill in the art that any suitable number of electrodes may be used. For instance, if the electrical energy is supplied as unipolar energy, a single electrode may be used. In another example, if the electrical energy is supplied as bipolar energy, two or more electrodes may be used.

FIG. 7A to 7D show a loop 400 according to embodiments of the present invention. As depicted, the loop 400 is similar to the loop 20, with the difference that a sensor 425 is mounted to the body 421. In embodiments, the sensor 425 and the electrodes 423 may be disposed on the inner side of the body 421.

In embodiments, the sensor 425 may be mounted in the body 421 formed of dielectric material so that the sensor 425 may be electrically insulated from the electrode 423. The electrodes 423 and sensor 425 may move along the body 421 when the loop 420 curls/uncurls around the target tissue.

When the electrode(s) 423 and the sensor 425 curl around the circumferential tissue 5 of the renal artery, in embodiments, the electrode(s) 423 and the sensor 425 contact the circumferential tissue 5. For instance, the electrode(s) 423 may receive electrical energy such as RF energy and generate heat energy. The sensor 225 may measure the impedance of the electrodes 423 or the temperature of the circumferential tissue. The sensor 425 may be connected to the central controller 200 via a wire(s) that run through the catheter apparatus 100, where electrical power for the sensor 425 may be also delivered via a wire(s).

Information of the measured impedance or temperature may be transmitted to the memory 203 of the catheter system 300. In embodiments, the operator may diagnose the denervation process using the information. The power for delivering thermal energy may also be automatically controlled by the energy source generator 205 or the central controller 200 based on the information. It is noted that other types of sensor may be used to measure various quantities, where each quantity may indicate the status of the denervation process and provide guidance to the physician during operation.

FIG. 8 is a schematic diagram of a catheter, illustrating renal denervation using the catheter according to embodiments of the present invention As shown in FIG. 8, the distal portion 11 of the catheter is advanced into proximity of the patient's renal artery RA. The operator may operate the loop control 90 so that the loop 20 (or 420) including a plurality of electrodes 23 (or 423) may curl around the circumferential tissue 5 of the renal artery to thereby directly or indirectly contact the circumferential tissue of the renal artery RA. The electrodes 23 (or 423) may be positioned on a circumferential treatment zone along a segment of the renal artery RA. The electrodes 23 (or 423) may include a first electrode to deliver thermal energy to a first treatment zone of the renal artery RA a second electrode to deliver thermal energy to a second treatment zone of the renal artery RA.

In embodiments, each of the electrodes may deliver thermal energy to a different treatment zone, respectively or deliver thermal energy to the same treatment zone.

In embodiments, the loop 20 (or 420) may be electrically coupled to energy source generator 205 for delivery of a desired electrical energy to the electrodes 23 (or 423). In embodiments, the electrical energy may be thermal RF energy using Quantum Molecular Resonance (QMR). A frequency of the RF energy may be higher than or equal to 4 MHz and may destruct at least a portion of the circumferential tissue 5 of the renal artery RA. In embodiments, the temperature range of the electrodes 23 (or 423) during operation ranges from 60 degrees to 70 degrees.

In embodiments, the loop 20 (or 420) may supply electrical energy to the circumferential tissue 5 of the renal artery RA to cause renal denervation through the electrode 23 (or 423). The heat energy, which is generated by the electrodes 23 (423), may destruct a portion of the circumferential tissue of the renal artery, where the circumferential tissue may include at least one of a renal nerve RN, lymphatics and capillaries. This may be achieved via contact between the loop 20 (or 420) and the circumferential tissue 5 of the renal artery RA. In embodiments, during the denervation, an impedance of the electrode or a temperature of the circumferential tissue may be measured using the sensor 425.

FIG. 9 is a flow chart 900 illustrating exemplary steps that may be carried out to denervate renal nerves according to embodiments of the present invention. The process starts at step 902. At step 902, the loop 20 (or 420) that is positioned near a target tissue, such as circumferential tissue 5 of the renal artery RA. In embodiments, the loop 20 (or 420) may include one or more electrode 23 (or 423). Next, at step 904, the loop 20 (or 420) may be curled around the target tissue.

At step 906, energy may be delivered to the electrode 23, where the electrode 23 may convert the energy into heat energy. Then, at step 908, at least a portion of the target tissue may be denervated by the heat energy.

The apparatus and methods described herein can be used to treat not only hypertension, but also other suitable types of diseases, such as chronic renal diseases, cardiovascular disorders, cardiac arrhythmias, and clinical syndromes where the renal afferent activation is involved. Using the catheter in embodiments, as compared to percutaneous catheter and surgical instrumentation, the physician may treat the diseases in an easier and safer manner.

In the description, numerous details are set forth for purposes of explanation in order to provide a thorough understanding of the present invention. However, it will be apparent to one skilled in the art that not all of these specific details are required in order to practice the present invention.

Additionally, while specific embodiments have been illustrated and described in this specification, those of ordinary skill in the art appreciate that any arrangement that is calculated to achieve the same purpose may be substituted for the specific embodiments disclosed. This disclosure is intended to cover any and all adaptations or variations of the present invention, and it is to be understood that the terms used in the following claims should not be construed to limit the invention to the specific embodiments disclosed in the specification. Rather, the scope of the invention is to be determined entirely by the following claims, which are to be construed in accordance with the established doctrines of claim interpretation, along with the full range of equivalents to which such claims are entitled.

What is claimed is:

1. A catheter apparatus for renal denervation, comprising:
    a shaft having a distal end; and
    a loop disposed near the distal end and configured to emerge from the distal end of the shaft and curl around an artery and onto itself, and receive, via the shaft, energy to denervate at least a portion of the artery,
    wherein the loop includes:
        a body capable of bending to curl around an axis in a direction perpendicular to a longitudinal direction of the shaft such that an outer surface of the body is directly adjacent to or contacts an inner surface of the body as the loop emerges from the distal end, and contacting an entirety of an outer circumferential surface of the artery, and
        a plurality of electrodes disposed on an inner side of the body and configured to face the outer circumferential surface of the artery when curled around the artery, each of the plurality of electrodes having an elongated rectangular shape and a longitudinal axis of the rectangular shape extends along a longitudinal direction of the body, and
    wherein the plurality of electrodes are configured to deliver the energy to the outer circumferential surface of the artery.

2. The catheter apparatus of claim 1, wherein the plurality of electrodes are configured to convert the energy into heat energy.

3. The catheter apparatus of claim 1, wherein the plurality of electrodes are electrically isolated from each other.

4. The catheter apparatus of claim 1, wherein the body is made of elastic material.

5. The catheter apparatus of claim 1, wherein the plurality of electrodes are configured to receive radiofrequency (RF) current and include a first electrode configured to deliver the energy to a first treatment zone of the artery; and a second electrode arranged in parallel to the first electrode and configured to deliver the energy to a second treatment zone of the artery.

6. The catheter apparatus of claim 1, wherein a distal portion of the body has a round shape as the loop is unrolled.

7. The catheter apparatus of claim 1, further comprising an energy source generator configured to deliver the energy,
wherein the energy received by the loop is at least one selected from the group consisting of radio-frequency (RF) energy, electrical energy, and thermal energy.

8. The catheter apparatus of claim 7, wherein the energy is electrical energy, and wherein the electrical energy includes bipolar energy or unipolar energy.

9. The catheter apparatus of claim 1, further comprising a holder coupled to a proximal end of the shaft, wherein the holder includes a loop control configured to control a movement of the loop relative to the shaft.

10. The catheter apparatus of claim 9, further comprising a slider rotatably mounted on the holder, wherein a rotation of the slider relative to the holder controls a rotation of the loop relative to the shaft along a longitudinal axis of the shaft.

11. The catheter apparatus of claim 1, wherein the loop further includes a sensor electrically insulated from the plurality of electrodes and configured to sense at least one of an impedance of the plurality of electrodes or a temperature of the artery.

12. The catheter apparatus of claim 1, wherein the body is coated with insulating materials.

13. The catheter apparatus of claim 1, wherein the artery includes at least one of a renal nerve, lymphatics and capillaries.

14. The catheter apparatus of claim 1, wherein the body has an elongated rectangular shape and a distal portion of the body has a round shape as the loop is unrolled.

15. A method for renal denervation using the catheter apparatus of claim 1, comprising:
curling the loop around the outer circumferential surface of the artery;
receiving the energy, thereby causing the plurality of electrodes to convert the energy into heat energy; and
denervating at least a portion of the artery using the heat energy.

16. The method of claim 15, wherein the step of curling the loop includes introducing the loop through a percutaneous access site of a patient.

17. The method of claim 15, wherein the energy is at least one selected from the group consisting of radio-frequency (RF) energy, electrical energy, and thermal energy.

18. The method of claim 15, further comprising:
sensing an impedance of the electrode or a temperature of the artery through a sensor which is disposed on the loop.

19. The method of claim 15, wherein the step of denervating includes delivering the heat energy sequentially to the artery to the artery.

* * * * *